United States Patent [19]

Arney, Jr.

[11] Patent Number: 4,829,003

[45] Date of Patent: May 9, 1989

[54] PYROELECTRIC ENZYME DETECTOR

[76] Inventor: Lawrence H. Arney, Jr., 613A DeHort St., Blacksburg, Va. 24060

[21] Appl. No.: 901,428

[22] Filed: Aug. 28, 1986

[51] Int. Cl.⁴ .................. C12M 1/40; C12Q 1/00; C12N 11/14; G01N 27/26

[52] U.S. Cl. .................. 435/288; 204/403; 435/4; 435/176; 435/177; 435/817

[58] Field of Search ............ 435/3, 4, 174, 176, 435/177, 181, 817; 422/95; 204/403

[56] References Cited

U.S. PATENT DOCUMENTS

| | | | |
|---|---|---|---|
| 3,542,662 | 11/1970 | Hicks et al. | 435/817 X |
| 3,861,879 | 1/1975 | Taylor | 422/95 |
| 4,004,979 | 1/1977 | Ayrameas et al. | 435/181 X |
| 4,021,307 | 5/1977 | Mosbach | 435/12 |
| 4,431,507 | 2/1984 | Nankai et al. | 435/817 X |
| 4,476,005 | 10/1984 | Tokinaga et al. | 435/817 X |
| 4,547,280 | 10/1985 | Karasawa et al. | 435/4 X |
| 4,551,425 | 11/1985 | Zemel | 435/4 |

Primary Examiner—David M. Naff
Attorney, Agent, or Firm—Larson and Taylor

[57] ABSTRACT

A pyroelectric sensor is provided for detecting enzymes or enzymatic substrates in a liquid or gas stream. The sensor contains a laminate formed of a pyroelectric material sandwiched between upper and lower conducting means to act as electrodes. An electronic circuit means is connected to the conducting means to measure thermally induced electric current and an enzyme or enzymatic substrate is immobilized on a surface of one of the conducting means. The laminate is supported by a support means and a plate means rests on an upper surface of the supported laminate. The plate means has a longitudinal flow channel communicating with the upper surface for flow of a gas of liquid, and a recess for accommodating the electronic circuit means. Inlet and outlet means pass through the plate means and communicate with the flow channel.

9 Claims, 3 Drawing Sheets

PYROELECTRIC ENZYME DETECTOR

BACKGROUND OF THE INVENTION

This invention relates in general to the detection of enzymes or enzymatic substrates directly by measuring the thermal signals produced by their reaction on the surface of a pyroelectric material.

The detection and measurement of enzymes or enzyme substrates in biological fluids is a problem of considerable importance in the detection of disease conditions or the elucidation of metabolic pathways in animal and vegetable substances. Workers in this field have been challenged by the need to develop an analytical method or instrument that is sensitive and reliable as well as adaptable to the physical constraints that may be imposed upon an analytical technique to measure enzyme systems in biological fluids. Many approaches have been investigated, including the detection of temperature changes in the environment of an enzyme and substrate resulting from the heat of reaction between that pair. Others have tried to detect temperature changes with thermistors and other temperature sensing devices but the methods have lacked sensitivity. Pyroelectric gas sensors have been disclosed by Taylor, U.S. Pat. No. 3,861,879, and Zemel, U.S. Pat. No. 4,551,425. The Taylor invention is limited to a device for the detection of a particular gas and is specifically directed to the detection of carbon monoxide. The Zemel invention incorporates a heater in a pyroelectric substrate to desorb adsorbed substances and corrollates their detection from heat changes associated with change of state. Zemel also describes and claims application of his pyroelectric sensor for the detection of an enzyme or coenzyme by reaction with a corresponding enzyme or coenzyme bound to the sensor. The pyroelectric sensor of Zemel is found to possess less than desirable sensitivity. Pyroelectric sensors, such as those described by Zemel, experience shortcomings when the enzyme or coenzyme are insufficiently bound to the sensor or where the bonding process significantly deactivates the enzyme.

Workers in the field of enzyme or enzyme substrate detection have also been challenged by the problem of how to immobilize said enzyme or substrate on a detector without chemically deactivating either. Similarly, investigators have struggled with the problem of detecting enzyme substrate reactions using thermal sensors where the heat of the reaction between the enzyme and substrate is weak.

Nothing in the prior art satisfactorily discloses an operable pyroelectric sensor for enzyme detection or solves the problems discussed herein.

OBJECTS OF THE INVENTION

In response to the foregoing problems and disadvantages in the application of pyroelectric materials to the detection of enzymes and their substrates it is an object of the present invention to provide a pyroelectric sensor for the detection of a corresponding substrate in a gas or liquid stream, having an enzyme deposited and immobilized without significant deactivation on the pyroelectric surface.

A further object of this invention is to provide an improved pyroelectric sensor for detecting an enzyme in a gas or liquid stream such as a biological fluid having deposited and immobilized on the pyroelectric surface the substrate for said enzyme.

Yet another object of this invention is to provide a pyroelectric sensor of improved sensitivity having deposited thereon chemicals reactive to the products of reaction of enzyme/substrate components.

A further object of this invention is to provide a pyroelectric sensor of improved sensitivity by utilizing materials of preferred thermal conductivity.

Yet another object of the present invention is to provide an improved method to deposit an enzyme on the surface of a pyroelectric sensor in such a manner that the enzyme is immobilized without significant deactivation.

SUMMARY OF THE INVENTION

The foregoing objectives are accomplished through the following:

A pyroelectric sensor for detecting an enzyme or enzymatic substrate in a gas or liquid stream comprising:

a. a pyroelectric material;

b. first means, affixed to first face of said pyroelectric material, for conducting an electrical response from said pyroelectric material;

c. at least one reactant selected from the group consisting of an enzyme and an enzymatic substrate reactable respectively with a corresponding substrate or enzyme in a gas or liquid stream to produce a thermally detectable endothermic or exothermic reaction, said reactant being immobilized in contact with said first conductive means;

d. second means, affixed to second face of said pyroelectric material, for conducting an electrical response from said pyroelectric material;

e. electronic circuit means connected to said first and second conducting means to measure thermally induced electrical current from said pyroelectric material;

f. support means to contain said pyroelectric material.

To further summarize the invention, on one of the electrodes of a pyroelectric sensor one or more of an enzyme or enzymatic substrate is deposited and chemically immobilized thereon. The laminate of pyroelectric material sandwiched between said first and second conducting means is installed in a structure so designed as to permit a stream of gas or liquid containing the material to be detected to flow over the surface on which the enzyme or substrate is immobilized. An electrical connection is made from one electrode to the input of a current to voltage converter and thence to a voltage amplifier so as to allow analog scaling of the signal. The second electrode of the laminate is connected to ground using a suitable conductor. In this way the material to be detected reacts with the reactant deposited on the electrode to produce a heat of reaction subsequently detectable as current flow in a pyroelectric material.

In another embodiment of the present invention both a substrate or enzyme and a chemical reactant reactable with the reaction products of a substrate/enzyme system are deposited on the electrode adjacent the zone where that specific substrate or enzyme reaction produces a heat of reaction insufficient to measure with accuracy. The heat of reaction between the enzyme/substrate reaction products and the deposited chemical will enhance the thermal signal of the overall reaction and increase the electrical signal from the pyroelectric material to a level more readily detectable with accuracy.

A further embodiment of this invention utilizes a support structure constructed from materials characterized by low thermal conductivity and high heat capacity. Such materials provide a minimum heat sink for the thermal signal produced by the enzyme substrate reaction and thereby does not deleteriously affect the detection of that signal.

DESCRIPTION OF THE PREFERRED EMBODIMENTS

Figure 1:
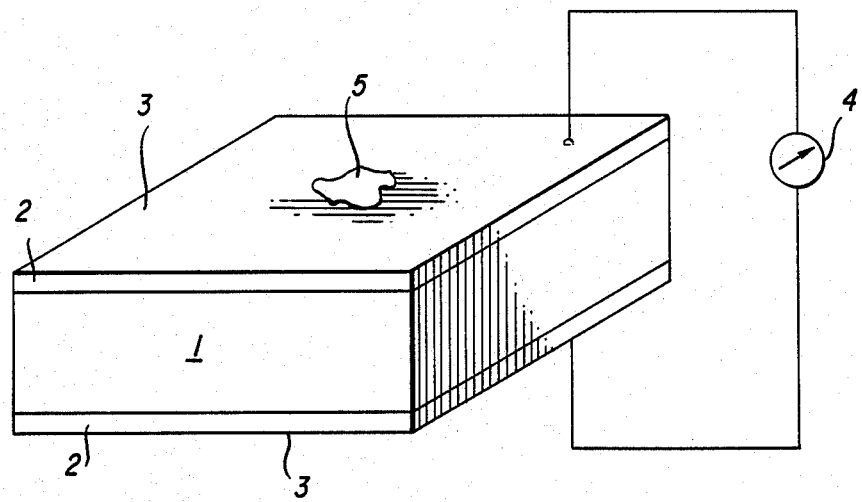
FIG. 1 is a perspective view of the pyroelectric sensor of the invention.

Referring now to the drawings and with specific reference to FIG. 1, a layer of pyroelectric material 1 such as polyvinylidene flouride (PVD) is coated on its top and bottom sides with aluminum 2. It should be understood that any pyroelectric material can be employed in this invention and any electrically and thermally conductive metal may be used in place of aluminum to act as electrodes.

In order to electrolytically protect the aluminum electrodes a small quantity of gold film 3 is sputtered onto and over the surface of the aluminum. The electrodes are connected to a suitable converter source 4 to convert the current to voltage and to amplify the voltage for measurement. A reactant such as enzyme 5 is deposited and immobilized on to one surface of the sensor for subsequent reaction with the material to be detected, in this case an enzymatic substrate. The enzyme deposited and immobilized pursuant to the present invention can be any enzyme known to react with enzymatic substrates to produce a thermal change. Illustrative of such an enzyme are catalase, urease, carbonic anhydrase, arginase, allantolase and the like.

Where it is desired to detect and/or measure the concentration of an enzyme in a gas or liquid stream, an enzymatic substrate specific to the enzyme is deposited and immobilized on the electrode. Thus, the substrate or a derivative thereof must be chemically immobilizable. Suitable enzymatic substrates or derivatives thereof include urea for the detection of urease, peroxides for the detection of catalase, etc.

As aforementioned, where the thermal effect of an enzyme/enzyme substrate reaction is low, its detection can be enhanced by causing the products of reaction between said enzyme and substrate to react with a chemical entity or reactant deposited on the same electrode adjacent to the reactant enzyme or substrate. The chemical reactant can be any chemical capable of reacting with enzyme/enzymatic substrate reaction products to produce a thermal change. For example, urease can be deposited on said electrode for reaction with urea present in a liquid stream. The reaction product, ammonia, subsequently reacts with an aldehyde deposited adjacent to the urease, preferably downstream of the enzyme/substrate reaction zone on the electrode. The strong ammonia-aldehyde reaction increases the thermal signal from the urease-urea reaction. The reactive aldehyde may be benzaldehyde or a polymeric molecule containing aldehyde functionality such as polyacrolein.

While there are a variety of methods available to immobilize enzymes and substrates on electrode surfaces the preferred approach in the context of this invention is to employ an aldehyde such as gluteraldehyde when immobilizing the enzymes. Gluteraldehyde reacts to crosslink the enzyme and establish immobility without significantly reducing enzyme activity. To achieve this, the immobilization reaction should be conducted between $-10$ and $+10°$ C. an the reaction quenched after approximately 10 minutes. The quenching can be effected by using an amino acid or other compounds containing primary amine groups.

Figure 2:
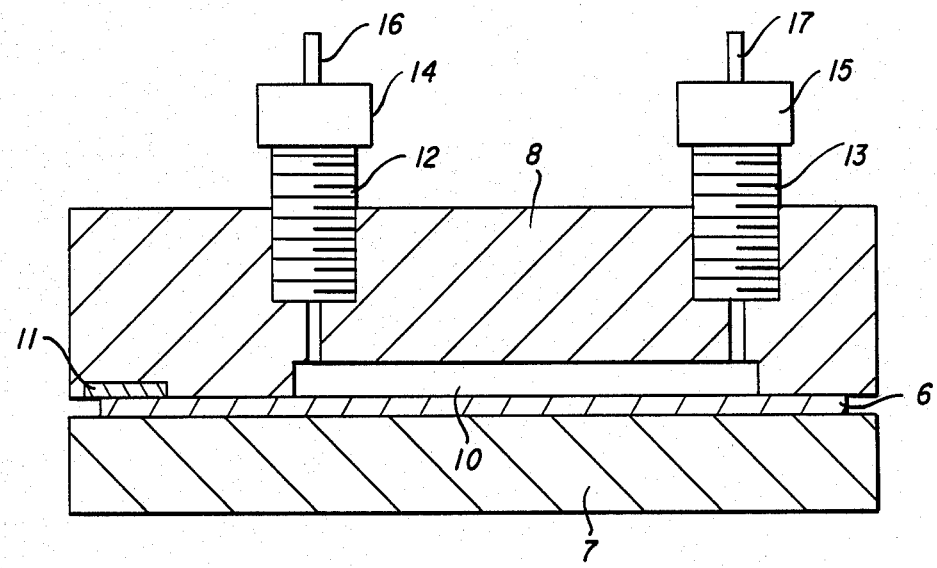
FIG. 2 is a side view of the support structure with the pyroelectric laminate installed thereon.
Figure 3:
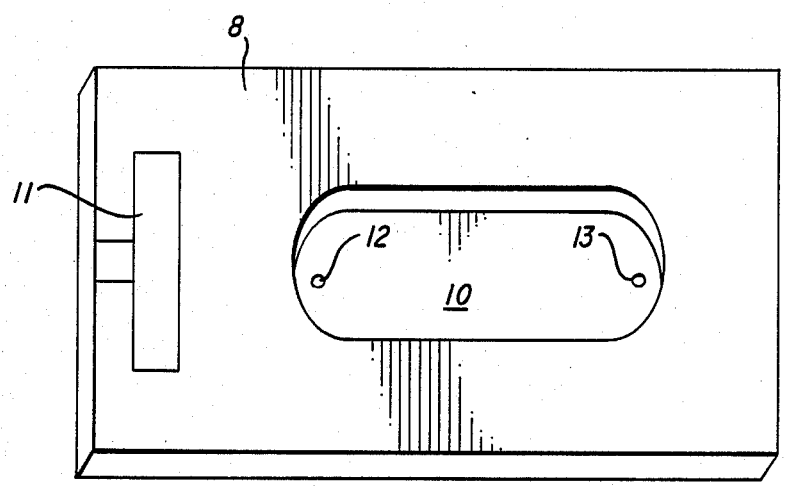
FIG. 3 is a top view of the interior of the support structure.
Figure 4:
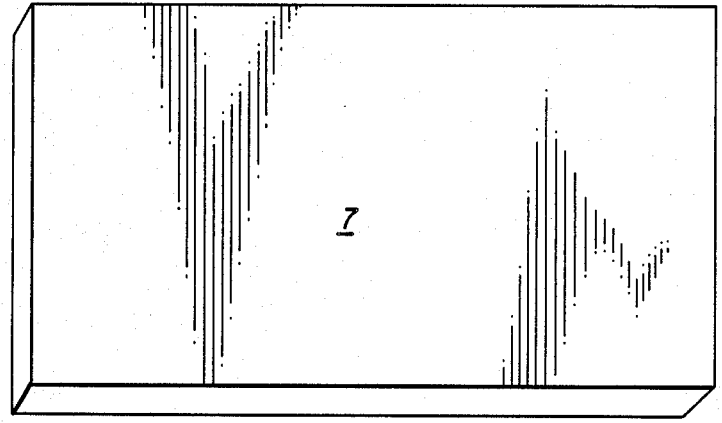
FIG. 4 is a perspective view of the backing of the support structure.

As shown in FIGS. 2 and 3 the resulting pyroelectric laminate of pyroelectric material sandwiched between said first and second conducting means 6 is placed in a support structure comprising a flat backing member 7 (see also FIG. 4) on which the laminate 6 is supported and an upper plate 8 (see also FIG. 3) which rests on the laminate 6. The upper plate 8 includes a milled flow channel 10 which is disposed directly above laminate 6 and a milled recess 11 for accomodating the connections to the laminate 6. Flow channel 10 communicates with orthogonal inlet passages 12 and 13 formed in the plate 8 and adapted at the upper ends thereof to receive respective threaded inlet and outlet tubing connectors 14 and 15 therein. Connectors 14 and 15 are connected to an inlet tube 16 and an outlet tube 17, respectively. A liquid or gas stream containing an enzymatic substrate is introduced through the inlet tube 16 into the flow channel 10 in the interior surface of plate 8 in contact with the pyroelectric laminate 6 and exits through the outlet tube 17.

A further advantage provided by the pyroelectric sensor of the invention is that it can be cut and formed into a variety of shapes permitting a high degree of manufacturing flexibility and ease of application. Accordingly, the ability to vary the electrode material as well as the pyroelectric material offered by the sensor is deemed an important advantage of this invention.

The following example is included to illustrate the construction and utilization of one embodiment of this invention.

EXAMPLE

The following example is included to illustrate the construction and utilization of one embodiment of this invention.

Figure 5:
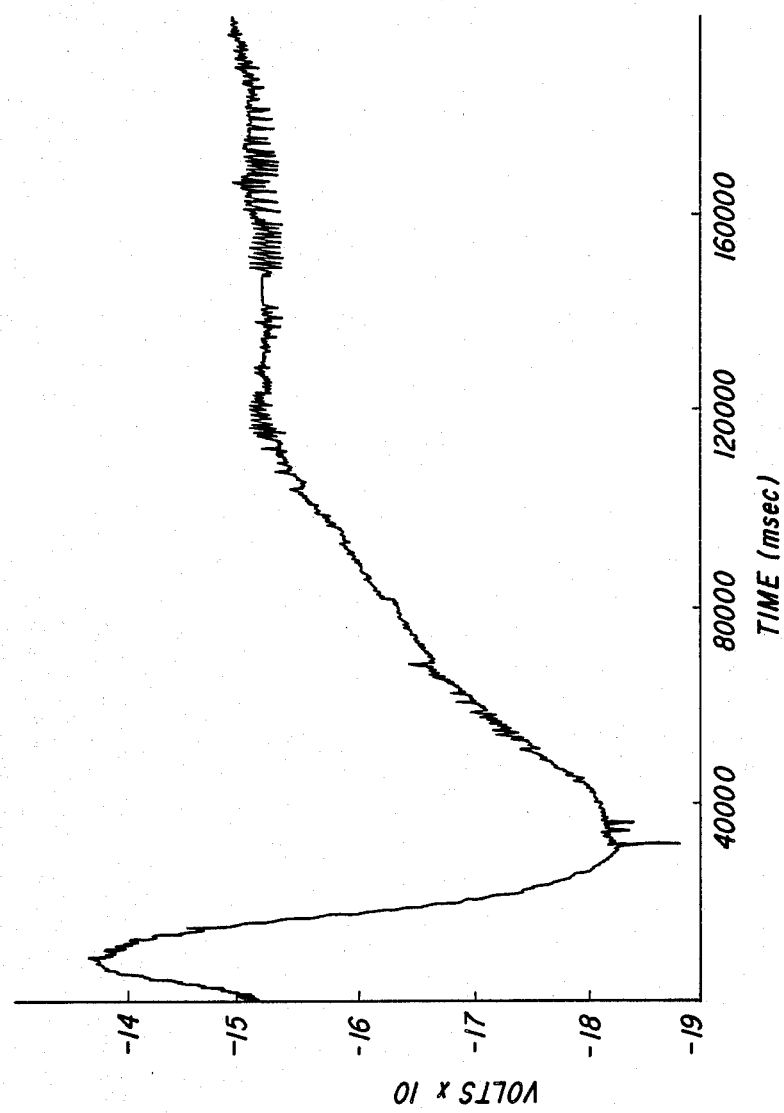
FIG. 5 is a diagram illustrating the voltage temperature response for an enzyme/substrate analysis.

Aluminum coated polyvinylidene fluoride pyroelectric film is obtained from a commercial source and cut to the desired size using caution to keep the film clean. Care should also be exercised to avoid one electrode folding around to the other electrode. One electrode surface is coated by sputtering thereon approximately 100 Angstroms of gold. 5 Milligrams of catalase is mixed well with 35 milligrams of bovine serum albumin and 200 microliters of water and the mixture is chilled to approximately 8° C. 20 Microliters of glutaraldehyde are then added to the resulting solution and the solution is spread over the gold-coated aluminum electrode surface. The crosslinking reaction is allowed to proceed for approximately 10 minutes and the sensor is then rinsed with a glycine solution. The thus prepared pyroelectric sensor is placed in the support structure shown in FIG. 2 and electrical leads attached as shown and approximately 50 microliters of a 0.093 molar solution of hydrogen peroxide is allowed to flow over the gold surface. The output from the electrode connections are recorded on a logging device through a current to voltage converter and voltage amplyfier. The results are reported in FIG. 5 and show a significant voltage difference detected within 40,000 milliseconds, indicative of a strong catalase peroxide reaction.

Various modifications of the pyroelectric enzyme sensor described above will be apparent to those of ordinary skill in the art and are embraced by the scope of the following claims.

What is claimed is:

1. A pyroelectric sensor for detecting an enzyme or enzymatic substrate in a gas or liquid stream comprising:
   (a) a pyroelectirc laminate having an upper and lower surface comprised of a pyroelectric material sandwiched between upper and lower conducting means to act as electrodes for conducting an electrical response from said pyroelectric material;
   (b) electronic circuit means connected to said electrodes to measure thermally induced electric current from said pyroelectric material;
   (c) a reactant selected from the group consisting of an enzyme and an enzymatic substrate reactable respectively with a corresponding enzyme or substrate to produce a thermally detectable endothermic or exothermic reaction, said reactant being chemically immobilized on a surface on one of said conducting means;
   (d) a support means supporting said laminate;
   (e) a plate means resting on the upper surface of said supported laminate, said plate means having a longitudinal flow channel for said gas or liquid stream disposed above and communicating with the upper surface of said laminated and said plate and means having a recess communicating with said upper surface for accomodating said electronic circuit means;
   (f) an inlet means passing through said plate means communicating with said flow channel near one end thereof; and
   (g) an outlet means passing through said plate means communicating with said flow channel near an end opposite said inlet means.

2. A pyroelectric sensor according to claim 1 wherein the reactant is an enzymatic substrate.

3. A pyroelectric sensor according to claim 1 wherein the reactant is an enzyme.

4. A pyroelectric sensor according to claim 1 wherein said support means is a material of high heat capacity and low thermal conductivity.

5. A pyroelectric sensor according to claim 4 wherein said support means is a thermoplastic or thermosetting resinous material.

6. A pyroelectric sensor according to claim 5 wherein said support means material is styrofoam.

7. A pyroelectric sensor according to claim 4 wherein said support means is a glass material.

8. A pyroelectric sensor according to claim 1 wherein said upper and lower conducting means is a metal.

9. A pyroelectric sensor according to claim 1 including a chemical entity in contact with one of said conducting means reactively responsive to reaction products of said group of an enzyme or an enzymatic substrate to provide a detactable thermal signal.

* * * * *